(12) United States Patent
White et al.

(10) Patent No.: US 7,236,936 B2
(45) Date of Patent: Jun. 26, 2007

(54) SECURITY INFUSION PUMP WITH BAR CODE READER

(75) Inventors: Gale White, Ft. Worth, TX (US); Ruth Kummerlen, Frisco, TX (US); Charlotte Ray, Fort Worth, TX (US); Roberta Stavely, Carrollton, TX (US); Michael Zakrewski, Carrollton, TX (US); Roger Hill, Richardson, TX (US)

(73) Assignee: B. Braun Medical, Inc., Bethlehem, PA (US)

( * ) Notice: Subject to any disclaimer, the term of this patent is extended or adjusted under 35 U.S.C. 154(b) by 562 days.

(21) Appl. No.: 10/334,659

(22) Filed: Dec. 30, 2002

(65) Prior Publication Data
US 2003/0139701 A1 Jul. 24, 2003

Related U.S. Application Data

(62) Division of application No. 09/452,488, filed on Dec. 1, 1999, now Pat. No. 6,519,569.

(51) Int. Cl.
*A61B 5/00* (2006.01)
(52) U.S. Cl. .......................................... 705/3; 604/151
(58) Field of Classification Search ................ 604/151, 604/181, 48, 186–187; 705/3; 700/3–5
See application file for complete search history.

(56) References Cited

U.S. PATENT DOCUMENTS

| 3,715,570 A | 2/1973 | Weichselbaum et al. |
| 3,826,900 A | 7/1974 | Moellering |
| 3,831,006 A | 8/1974 | Chaffin, III et al. |
| 3,848,112 A | 11/1974 | Weichselbaum et al. |
| 4,121,574 A | 10/1978 | Lester |

(Continued)

FOREIGN PATENT DOCUMENTS

| CA | 2110774 | 6/1995 |
| EP | 0439355 | 7/1991 |
| GB | 2279784 | 1/1995 |
| WO | WO-89/08264 | 9/1989 |
| WO | WO-96/36923 | 11/1996 |
| WO | WO-99/10029 A1 | 3/1999 |
| WO | WO-00/03344 | 1/2000 |
| WO | WO-01/39816 | 6/2001 |
| WO | WO-01/88828 | 11/2001 |

OTHER PUBLICATIONS

Stobart et al., "An integrated hospital computer system", Systems Technology, Dec. 1978 No. 30.

(Continued)

*Primary Examiner*—Melissa A McCorkle
(74) *Attorney, Agent, or Firm*—Osha Liang LLP; John W. Montgomery (57) ABSTRACT

A medical infusion pump with a bar code reader having simplified and enhanced security features. The infusion pump with bar code reader is comprised of an infusion pump with a housing, a control display screen and control software for operating the infusion pump according to input infusion data. A bar code reader is contained in the infusion pump housing and operatively attached to communicate scanned bar code infusion data to the pump display screen and to the control software. At least one initialization button for starting execution of a bar code scanning program is operatively connected through circuitry in the pump, the program activating the bar code reader to scan for an authorized user code, for an authorized user ID code, for a patient ID code, and for infusion data compatible for operating the infusion pump. A confirmation program and confirmation buttons manually operable by the authorized user. Acceptable scanning of authorization code, authorized user ID code, patient ID code and infusion data must be manually confirmed by the authorized user prior to activating the pump to infuse fluids according to the infusion data.

7 Claims, 6 Drawing Sheets

U.S. PATENT DOCUMENTS

| | | | |
|---|---|---|---|
| 4,164,320 A | 8/1979 | Irazoqui et al. | |
| 4,308,866 A | 1/1982 | Jelliffe et al. | |
| 4,373,527 A | 2/1983 | Fischell | |
| 4,443,218 A | 4/1984 | DeCant, Jr. et al. | |
| 4,476,381 A | 10/1984 | Rubin | |
| 4,543,955 A | 10/1985 | Schroeppel | |
| 4,573,994 A | 3/1986 | Fischell et al. | |
| 4,628,193 A | 12/1986 | Blum | |
| 4,706,207 A | 11/1987 | Hennessy et al. | |
| 4,731,051 A | 3/1988 | Fischell | |
| 4,756,706 A | 7/1988 | Kerns et al. | |
| D297,939 S | 10/1988 | Bradbury et al. | |
| 4,814,759 A | 3/1989 | Gombrich et al. | |
| 4,818,850 A | 4/1989 | Gombrich et al. | |
| 4,831,562 A | 5/1989 | McIntosh et al. | |
| 4,835,372 A | 5/1989 | Gombrich et al. | |
| 4,847,764 A | 7/1989 | Halvorson | |
| 4,850,009 A | 7/1989 | Zook et al. | |
| 4,853,521 A | 8/1989 | Claeys et al. | |
| 4,857,713 A | 8/1989 | Brown | |
| 4,857,716 A | 8/1989 | Gombrich et al. | |
| 4,916,441 A | 4/1990 | Gombrich | |
| 4,925,444 A | 5/1990 | Orkin et al. | |
| 4,978,335 A * | 12/1990 | Arthur, III | 604/67 |
| 4,991,091 A | 2/1991 | Allen | |
| 5,006,699 A | 4/1991 | Felkner et al. | |
| 5,049,047 A | 9/1991 | Polaschegg et al. | |
| 5,078,683 A | 1/1992 | Sancoff et al. | |
| 5,104,374 A | 4/1992 | Bishko et al. | |
| 5,153,416 A | 10/1992 | Neeley | |
| 5,153,827 A * | 10/1992 | Coutre et al. | 604/111 |
| 5,179,569 A | 1/1993 | Sawyer | |
| 5,195,123 A | 3/1993 | Clement | |
| 5,207,642 A | 5/1993 | Orkin et al. | |
| 5,213,232 A | 5/1993 | Kraft et al. | |
| 5,213,483 A | 5/1993 | Flaherty et al. | |
| 5,272,318 A | 12/1993 | Gorman | |
| 5,272,321 A | 12/1993 | Otsuka et al. | |
| 5,291,399 A | 3/1994 | Chaco | |
| 5,292,029 A | 3/1994 | Pearson | |
| 5,307,372 A | 4/1994 | Sawyer et al. | |
| 5,314,243 A | 5/1994 | McDonald et al. | |
| 5,317,506 A | 5/1994 | Coutre et al. | |
| 5,319,363 A | 6/1994 | Welch et al. | |
| 5,348,008 A | 9/1994 | Bornn et al. | |
| 5,368,562 A | 11/1994 | Blomquist et al. | |
| 5,373,527 A | 12/1994 | Taniu et al. | |
| 5,374,813 A | 12/1994 | Shipp | |
| 5,378,231 A | 1/1995 | Johnson et al. | |
| 5,392,638 A | 2/1995 | Kawahara | |
| 5,416,695 A | 5/1995 | Stutman et al. | |
| 5,445,621 A * | 8/1995 | Poli et al. | 604/246 |
| 5,451,760 A | 9/1995 | Renvall | |
| 5,465,082 A | 11/1995 | Chaco | |
| 5,505,696 A | 4/1996 | Miki | |
| 5,536,084 A | 7/1996 | Curtis et al. | |
| 5,542,420 A | 8/1996 | Goldman et al. | |
| 5,544,661 A | 8/1996 | Davis et al. | |
| 5,564,429 A | 10/1996 | Bornn et al. | |
| 5,582,593 A | 12/1996 | Hultman | |
| 5,594,786 A | 1/1997 | Chaco et al. | |
| 5,597,995 A | 1/1997 | Williams et al. | |
| 5,626,151 A | 5/1997 | Linden | |
| 5,630,710 A | 5/1997 | Tune et al. | |
| 5,640,301 A | 6/1997 | Roecker et al. | |
| 5,643,212 A | 7/1997 | Coutre et al. | |
| 5,658,250 A | 8/1997 | Blomquist et al. | |
| 5,697,899 A | 12/1997 | Hillman et al. | |
| 5,700,998 A | 12/1997 | Palti | |
| 5,713,856 A | 2/1998 | Eggers et al. | |
| RE35,743 E | 3/1998 | Pearson | |
| 5,732,401 A | 3/1998 | Conway | |
| 5,735,263 A | 4/1998 | Rubsamen et al. | |
| 5,755,357 A | 5/1998 | Orkin et al. | |
| 5,781,442 A * | 7/1998 | Engleson et al. | 700/214 |
| 5,797,515 A | 8/1998 | Liff et al. | |
| 5,800,383 A | 9/1998 | Chandler et al. | |
| 5,800,387 A | 9/1998 | Duffy et al. | |
| 5,822,544 A | 10/1998 | Chaco et al. | |
| 5,840,026 A | 11/1998 | Uber, III et al. | |
| 5,845,264 A | 12/1998 | Nellhaus | |
| 5,852,590 A | 12/1998 | De La Huerga | |
| 5,865,745 A | 2/1999 | Schmitt et al. | |
| 5,871,465 A | 2/1999 | Vasko | |
| 5,883,576 A | 3/1999 | De La Huerga | |
| 5,912,818 A | 6/1999 | McGrady et al. | |
| 5,939,699 A | 8/1999 | Perttunen et al. | |
| 5,945,651 A | 8/1999 | Chorosinski et al. | |
| 5,960,085 A | 9/1999 | De La Huerga | |
| 6,003,006 A | 12/1999 | Colella et al. | |
| 6,031,621 A | 2/2000 | Binder | |
| 6,068,156 A | 5/2000 | Liff et al. | |
| 6,070,761 A | 6/2000 | Bloomo et al. | |
| 6,078,273 A | 6/2000 | Hutchins et al. | |
| 6,082,776 A | 7/2000 | Feinberg | |
| 6,110,152 A * | 8/2000 | Kovelman | 604/232 |
| 6,116,461 A | 9/2000 | Broadfield et al. | |
| 6,123,686 A | 9/2000 | Olsen et al. | |
| 6,150,942 A | 11/2000 | O'Brien | |
| 6,152,364 A | 11/2000 | Schoonen et al. | |
| 6,170,746 B1 | 1/2001 | Brook et al. | |
| 6,213,972 B1 | 4/2001 | Butterfield et al. | |
| 6,230,927 B1 | 5/2001 | Schoonen et al. | |
| 6,234,997 B1 | 5/2001 | Kamen et al. | |
| 6,241,704 B1 | 6/2001 | Peterson et al. | |
| 6,256,967 B1 | 7/2001 | Hebron et al. | |
| 6,259,654 B1 | 7/2001 | De La Huerga | |
| 6,283,322 B1 | 9/2001 | Liff et al. | |
| 6,317,719 B1 | 11/2001 | Schrier et al. | |
| 6,321,203 B1 | 11/2001 | Kameda | |
| RE37,531 E | 1/2002 | Chaco et al. | |
| 6,352,200 B1 | 3/2002 | Schoonen et al. | |
| 6,370,841 B1 | 4/2002 | Chudy et al. | |
| 6,464,667 B1 | 10/2002 | Kamen et al. | |
| 6,493,747 B2 | 12/2002 | Simmon et al. | |
| 6,507,868 B2 | 1/2003 | Simmon et al. | |
| 6,519,569 B1 | 2/2003 | White et al. | |
| 6,779,024 B2 | 8/2004 | DeLaHuerga | |
| 6,796,956 B2 | 9/2004 | Hartlaub et al. | |
| 6,969,369 B2 | 11/2005 | Struble | |
| 2002/0026330 A1 | 2/2002 | Klein | |
| 2002/0038392 A1 | 3/2002 | De La Huerga | |
| 2002/0084904 A1 | 7/2002 | De La Huerga | |
| 2002/0169636 A1 | 11/2002 | Eggers et al. | |

OTHER PUBLICATIONS

Hubbell, et al., "A Uniform Labeling System for Blood Services", Medical Instrumentation, vol. 15, No. 1, Jan.-Feb, 1981, pp. 61-63.

Richard Farb, "Bar Coding for Medical Device Labeling", MD&DI, Aug. 1983, pp. 27-29, 88.

Hokanson, et al., "Potential use of bar codes to implement automated dispensing quality assurance programs", Hospital Pharmacy, vol. 20, May 1985, pp. 327-333, 337.

EPO Proceeding Further with the European Patent Application Pursuant to Article 96(1) and Rule 51(1) EPC, Mar. 16, 2005, 4 pages.

EPO Communication Pursuant to Article 96(2) EPC, Jun. 28, 2005, 5 pages.

EPO Communication Pursuant to Article 96(2) EPC, Apr. 7, 2006, 4 pages.

EPO Decision to Refuse a European Patent Application, Jan. 8, 2007, 8 pages.

* cited by examiner

SECURITY INFUSION PUMP WITH BAR CODE READER

RELATED PATENTS AND APPLICATIONS

The present application is a Divisional application of U.S. application Ser. No. 09/452,488, filed Dec. 1, 1999 and issued Feb. 11, 2003 as U.S. Pat. No. 6,519,569, which is incorporated herein and relied upon for priority and all legitimate purposes.

TECHNICAL FIELD OF THE INVENTION

The present invention relates to a medical infusion pump with bar code reading capabilities, designed for use in a hospital or other healthcare institution or facility. The medical infusion pump with the bar code reader also forms a part of a patient care system. The invention relates particularly to labeling the containers not only with human readable printed label information but also with corresponding bar code information and to an infusion pump having an optional bar code reading mechanism and computer program system incorporated with the pump to optionally permit authorized healthcare personnel and particularly nurses to either scan the information into the pump or to manually enter the information through a control panel.

BACKGROUND OF THE INVENTION

Modern healthcare, particularly in hospitals, clinics and other healthcare institutions, has improved and benefited significantly from the development and use of medical infusion pumps to enhance patient care. For example, parenteral infusion directly into the patient and, in particular, intravenous infusion directly into the patient's circulatory system, can be advantageous. Therapeutic fluids, drugs, medications, pharmacological fluids, hydrating fluids, sucrose fluids, nutrient fluids, or other therapeutic fluids can generally be infused using disposable cassette pumps and peristaltic pumps. Syringe pumps can also be used in some instances. Particularly, it is advantageous to provide different kinds of controlled infusion including rate controlled infusion, periodic infusion, and bolus dosage infusion, all depending upon the medication, the patient, the patient's condition and any of a number of other healthcare considerations.

In institutional healthcare facilities, such as major hospitals, large clinics and other institutional healthcare facilities, prescribed medications are prepared by a staff pharmacist or a team of pharmacists, according to a doctor's order. Detailed instructions for the administration of the drug shall be provided also according to the professional knowledge of the pharmacist with respect to pharmacological protocol for the medication or drugs involved. The medication is received by a nurse or a medical technician in an appropriate container prepared by the pharmacist to be delivered to the patient's room and accordingly administered to the patient. For purposes of accurate infusion, rather than merely using a timed drip-type infusion mechanism, infusion pumps are beneficially used. Based upon the prescribed medication, the protocol for administering the modern infusion therapeutic fluid may include carefully controlled infusion rates. Modern infusion pumps may be adjustably configured by the person administering the infusion to deliver the fluid according to the doctor's and/or pharmacist's instructions.

In order to facilitate management and accuracy of infused medication, various systems have been devised for purposes of providing certain drug information and/or patient information, either directly to the pump from the container of the medicinal fluid or to the pump from a central computer network to be interconnected with all infusion pumps throughout the medical institution or hospital. One such infusion fluid institutional management system provides an infusion pump having means for storing predetermined infusion data in a computer type memory. Such a prior system requires comparison of compatibilities of drugs, allergies of the patient, appropriate drug therapy, and patient conditions. This kind of complex comparison requires that a bar code label on the drug container is scanned and read into the computerized pumping system for automatically comparing the scanned clinical information to the data stored in memory for the infusion pump. The scanned and transferred data must be checked with the stored data for comparison and for prompting the operator to take action in response to discrepancies between the scanned data and the predetermined stored data. Although such a system provides certain measures of security to reduce certain kinds of manual entry errors through comparison of the bar code read data with a comprehensive data base of predetermined information in a large computer memory, it nevertheless includes certain complexities and fails to assure certain safeguards that might be accomplished without a central processor network and without a computer memory for storing comparison infusion data for numerous different drugs. There is a need for an optional system for scanned entry of basic infusion data having human accountability built in and without the associated complexity of prior systems.

SUMMARY OF THE INVENTION

To overcome certain deficiencies and to reduce certain complexities of prior bar code scanner infusion devices and systems, the present invention provides an infusion pump with a bar code scanner and a display for infusion data scanned from a bar coded label on a medicinal fluid container. The bar code scanning capability is selectively activated by an authorized user, such as an authorized nurse or other trained healthcare professional. Upon activation, the nurse is prompted to scan for an authorized user code and a nurse's ID code. As one alternative embodiment the nurse's ID code includes a special authorized user code. If the authorized user code is not scanned or the nurse's ID does not include the authorized user code, then the scanning mechanism is inactivated and will not operate for further scanning of patient ID code and drug infusion information. If the authorized user code is present, then the pump prompts the nurse to scan in the patient's ID. This patient ID is preferably scanned directly from a patient's wristband, ID card, badge, hospital chart or other device that provides the Patient's ID code and is purposefully secured to the patient while in the healthcare facility for treatment. If the patient ID information is not scanned, then the scanning mode again becomes inactivated and manual input of infusion data and patient information will be required. When the patient ID is properly scanned, then the nurse is prompted to scan information, including intended patient ID, medication name and infusion instructions from the pharmaceutical fluid container, whether a bag, a bottle, a syringe or another container. These containers are provided with a bar code label identifying the intended patient, the drug name, the concentration, concentration volume, volumes to be delivered, infusion rates, the patient's height and the patient's weight, as may be applicable. The drug infusion data is in accordance with a doctor's written order for medication or other therapy and also as established by a staff pharmacist who prepares a bar code label that is capable of being read by a bar code reader operatively coupled to a pump according to the present invention. The bar code format for the label and for the pump bar code reader should be compatible throughout a given medical facility. Preferably, the label also provides the information in human readable format along with the bar code.

Upon reading information from the label of the container of medicinal fluid, pump control software displays an appropriate display of the name of the drug identified by the bar code label. The software further captures the concentration, concentration volume, volume to be delivered and infusion rate, if not calculated. It will be understood that in certain instances the physician and the pharmacist may specify the infusion rate directly so that it might not be necessary to provide infusion data from which the rate would otherwise be calculated by sophisticated pump software. Thus the concentration, dosage, patient height and patient weight is also provided, if applicable for purposes of calculating the infusion rate. The patient's name or patient's ID number is also provided in bar code format and other important patient information could be additionally provided. The pump software will require that an authorized nurses ID has been scanned and that the scanned patient ID matches the patient ID on the label. Certain items of required infusion information are displayed for the nurse to view on a visual display. The nurse then must validate required displayed items of input, including the drug name, the concentration, the concentration volume, the volume to be delivered and the infusion rate. If all of the required infusion information is validated by the nurse, then the infusion may be initiated according to the accurately scanned infusion information such as the volume to be delivered and infusion rate that is read directly from the infusion information bar code label on the fluid container and into a software control program of the infusion pump. If any of the required information cannot be accurately validated by the nurse, then the scan mode is exited and the nurse must manually input the required data and infusion rates into the pump software control program using control panel buttons, toggles and displays.

Because the nurse's ID must be scanned into the system before the bar code reading can be initiated and also because the patient's ID must be successfully scanned and verified as matching the patient ID on the bar code label by the infusion pump comparison process, the system is provided with safeguards not present in other systems. Having the nurse's identification scanned and recorded in the pump software, causes the nurse's validation of the scanned input information to be a meaningful exercise for which human responsibility is established. The authorization code that the nurse's ID has provided also insures that the infusion setup using a bar code scanned infusion data will be initiated only by responsible identified professionals. The scanning and confirmation of the patient's ID from a wristband, a patient ID card, a patient badge or patient chart will increase the accuracy of delivering the appropriate medications to the proper patient. Preparation of the both the medicine and the labels by pharmacist maintains current safeguards and confirmation the of information by the comparison process and by the authorized and identified nurse further increases the security of the system.

As set forth in greater detail below, a new bar code reading system is provided having a medical infusion pumping device, bar code scanning hardware connected to the medical infusion pumping device, pump software and software to create a label with appropriate bar coding and a label for containers of medical fluids with the appropriate bar code information on the label. The system provides the user with an optional method of infusion data input. Existing medical infusion devices provide for manual keyboard and display programming for medical infusion protocol and administration instructions for the infusion device. The new system has additional components that provide an optional method for inputting medical infusion data that is useful at healthcare facilities to reduce the risk of incorrect infusion data and to automate and speed the infusion of a variety of fluids for patients. Preferably the bar code reader is contained within the infusion device and will capture data from an infusion container appropriately labeled for the pump-specific control software. An authorized healthcare professional will be identified as part of the bar code reading sequence, the patient will be similarly identified as part of the bar code reading sequence and the authorized and identified healthcare professional will validate that all scanned parameters were captured correctly and only then will the pump be activated to deliver fluid to the patient. The parameter to be captured on the bar code label and transferred to the pump can include patient identification number, drug name, concentration and concentration volume, volumes to be delivered, rates of delivery (if not calculated from concentration, volume and dose), dosage data (if not calculated from concentration, volume and rate), patient weight, weight unit, patient height and height unit. All scanned entries can be recorded in memory or printed for quality control review and for use to assist a physician in performing appropriate future treatment.

BRIEF DESCRIPTION OF THE DRAWINGS

These and other objects and advantages of the invention will be more fully understood with reference to the specifications, claims and drawings in which like numerals represent like elements and in which:

DETAILED DESCRIPTION OF THE PREFERRED EMBODIMENTS

Figure 1:
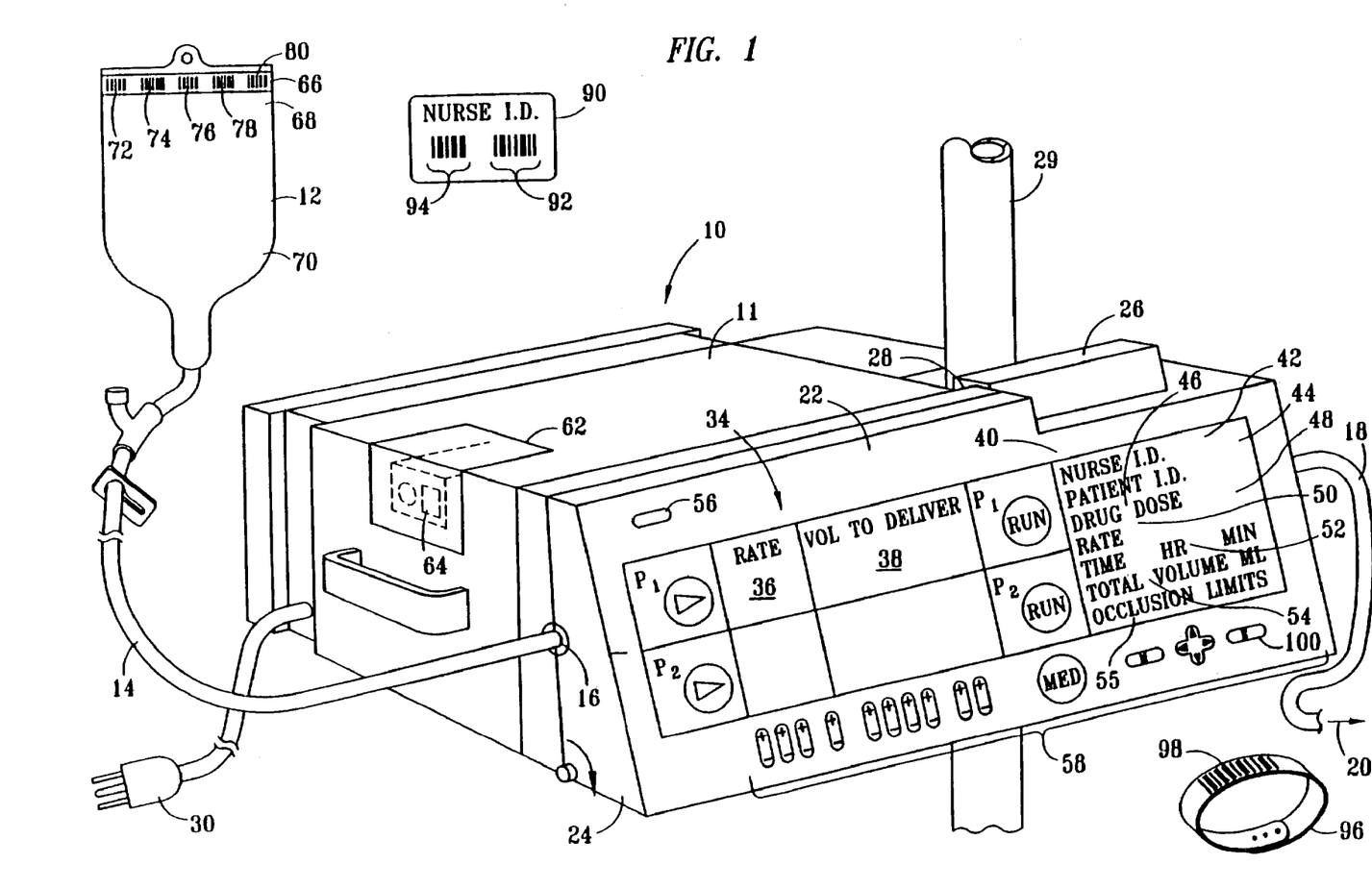
FIG. 1 is a schematic perspective view of a bar code reading and infusion pumping device according to one embodiment of the present invention.

FIG. 1 shows a schematic perspective view of a bar code reading infusion pumping device 10 according to one aspect of the present invention. In this embodiment the pumping device 10 and its various components are generally enclosed within a housing 11. The pumping device works together with a medicinal fluid to be pumped provided from a container 12 that may be a medical bottle or disposable fluid bag or other container capable of holding the required medicinal fluid and appropriately interfacing with the pumping device 10 to provide the fluid to the patient. Fluid from the container 12 is provided through input tube 14 that may be appropriate plastic or medical grade PVC or silicon tubing. Although a cassette pump is depicted in FIG. 1, it will be understood that principles of bar code scanning, according to the present invention, may similarly be applicable to the linear peristaltic pump or other appropriate modes of pumping. The tubing carries the fluid into the pumping device through access opening 16 that may lead to a disposable pumping cassette as set forth and described in U.S. Pat. Nos. 5,302,093 and 5,554,013 incorporated by reference herein or alternatively, may be engaged in a peristaltic pumping mechanism such as the linear peristaltic pumping mechanism of U.S. Pat. Nos. 5,660,529 and 5,888, 052 incorporated herein by reference.

As the fluid is actively moved through the pump, it is carried to a patient schematically represented by arrow 20 through an IV tubing 18. Control of the pump rate pumping volume, pumping time and safety limitations is generally addressed through a control panel 22. The control panel in FIG. 1 is hingably connected and swings open as indicated at 24 to accept replaceable cassettes (or in the case if a linear peristaltic pump, openable to accept and engage the PVC tubing 14 directly into the pumping mechanism). The pump door 24 is released using a release lever 26. The entire pumping mechanism is shown attached through a pole clamp 28 to a pump mounting pole 29. The pump is provided with power, preferably electrical power, schematically represented as an electrical plug 30. Other types of power, such as battery power and, particularly battery back-up systems may be appropriately included within the pump and the pump control hardware.

The pump is provided with a visual display panel 34 that is conveniently and advantageously formed on the control panel 22. This control panel 22 is provided with a visual display of adjustable pump-operating characteristics, including infusion rate display 36, volume to be delivered display 38 and a program infusion data display 40. Preferably, the program infusion data display 40 includes display capabilities for scannable bar code data, including nurse identification and/or number display 42, a patient identification name and/or number display 44, a drug name or other identification display 46, a dosage display 48, a rate display 50, a running time display 52, total volume of infusion display 54 and possibly other displays of limitations display 55, such as occlusion limits or other conditions, alarm or limitations that may be beneficial for signaling to the operator.

For purposes of operating the pump according to the present invention, a power switch or power button 56 is provided on the control panel and also a plurality of infusion data input controls schematically represented as buttons 58 are provided for manually entering rate, volume to be delivered, accessing a menu of drugs and options and toggling between various menu items, as well as entering available menu items. These menu items will typically include available drug information, rates and dosage and other pump control information programmed into onboard pump control software, all of which may be selected using a toggle or other mechanism and appropriately entered into the pump control software for operating the pumping mechanism.

According to the present invention, the pump housing 11 also carries an operably connected bar code scanner 62, having a scanner window 64 depicted on the side of the pumping housing 11, it being understood that the scanner window 64 might also be in another position or otherwise directed for usefulness of the pump, however in the embodiment depicted where a plurality of pumps 10 might be stacked one on top of the other, attached through pole clamps 28 to a pole 29, it is preferred to provide the scanning window 64 facing toward a side or toward the front. The side being advantageous as a position for the bar code scanning window because of the effective use of the front panel 22 for display and manual programming.

The bar code scanner 62 is useful with a container 12, having a pharmacist prepared therapeutic fluid 70 therein. The container is advantageously provided with a bar code label 66 and preferably also a human readable printed infusion data label 68 corresponding to the bar code information on bar code label 66. The operator may activate the scanning mode by using menu and cursor keys to activate a menu item. The pump will prompt the user to provide certain required information, including a scan of a nurse's ID badge 90. The nurse's ID badge 90 will preferably have an identification code number 92 and also an appropriate authorization code 94. Only with the authorization code and the nurse's ID can the scanning mode be continued. Subsequent to scanning in the nurse's ID, a patient ID must be scanned, as from a patient wrist band 96 or a patient ID card, having a bar code to identify the patient by name and/or by patient number. After the nurse's ID and the patient's ID are appropriately scanned and confirmed, as by using the "E" or "enter" button 100, then the bar code label 66 of the medication container 12 can also be scanned. Preferably, the bar code label on the medication container is prepared only by a pharmacist that also prepares the medicament 70. The infusion information will advantageously include the patient identification field 72, the drug name or identification 74, a dosage 76, a rate 78 and other infusion information 80, as may be appropriate. For purposes of further confirmation, all the requisite information may also be advantageously printed in a human readable label 68 corresponding to the bar code fields that are scanned for convenience and accuracy.

Figure 2:
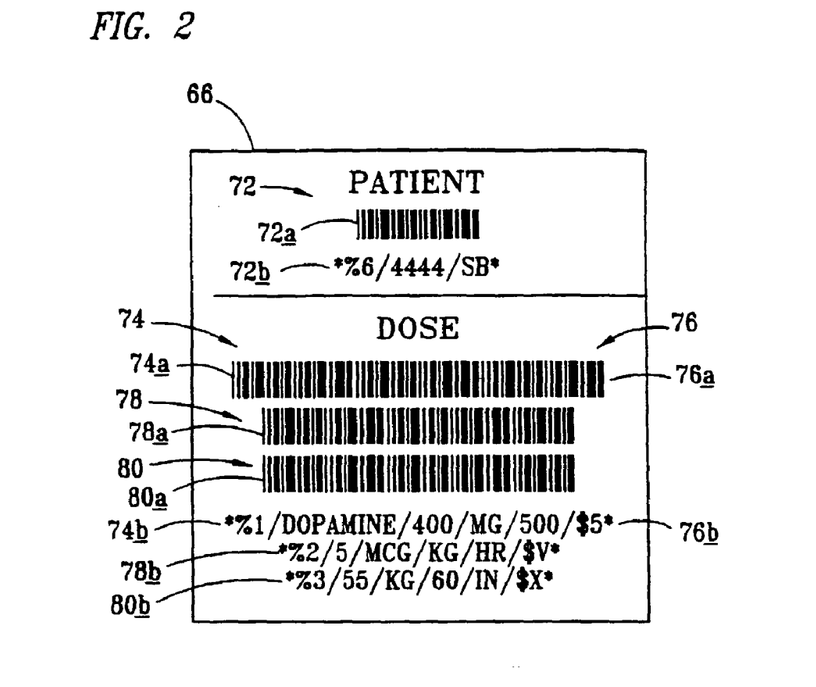
FIG. 2 is a schematic flow diagram of the bar code reading security system and the use of the bar code reading infusion pump according to the present invention.

FIG. 2 is a large schematic depiction of a sample bar code label 66 according to certain aspects of the present invention. On this label the patient field 72 is depicted with a bar code portion 72a and a numeric portion 72b by which the patient is identified according to the procedure of the healthcare facility. A drug identification field 74 and a dosage field 76 include both a drug identification bar code portion 74a and a drug identification alpha numeric portion 74b and also a bar code portion dosage 76a with a bar code alpha numeric portion 76b. An infusion rate 78 includes a bar code representation 78a as well as a alpha numeric representation 78b. Further depicted on the sample label 66 is a field 80 for other information and in this particular example, both weight and height information for the patient including a bar code representation of this information 80a and a alpha numeric representation 80b.

Figure 3A:
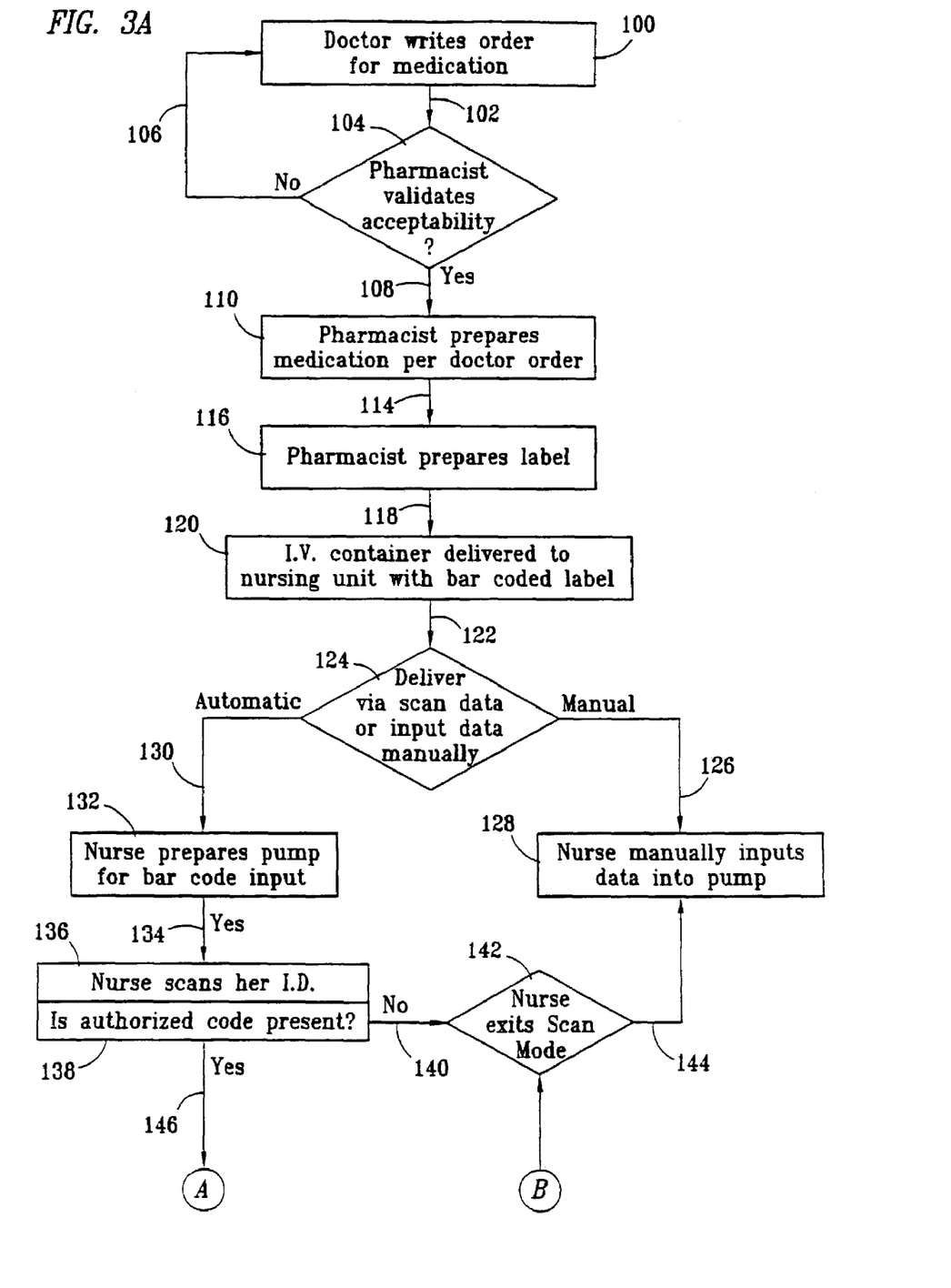
FIG. 3 is a schematic prospective view of a bar code reading module usefully incorporated into the infusion pumping device of the present invention.
Figure 3B:
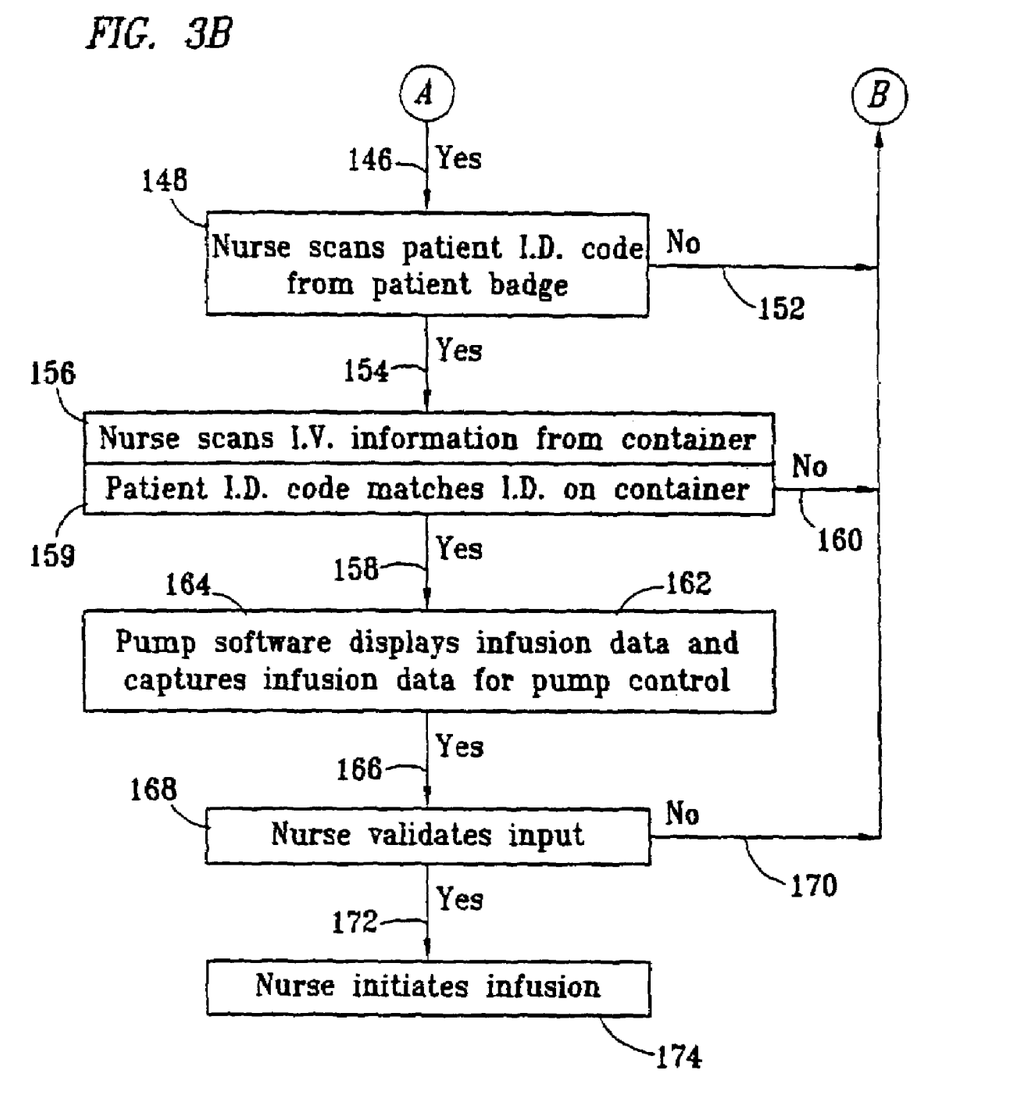

FIG. 3 is a schematic flow diagram of the operation of a bar code scanning pump in a system for improved accuracy and security using a bar code label and bar code reader for medications. In this flow diagram, the initial step is for the doctor to write an order for medication as at step 100. The order for the medication goes to a qualified pharmacist and, in particular, a pharmacist who prepares medications for the institution at which the infusion will be administered as indicated by arrow 102. In step 104 the pharmacist validates the acceptability of the medication ordered for a particular patient. If, for any of a number of reasons, the pharmacist believes that the medication is not acceptably written by the doctor, then the pharmacist sends the order back to the doctor, as indicated by arrow 106, so that the order may be rewritten to be acceptable to the pharmacist. In the event that the order is acceptable, then the pharmacist moves to the next step, as indicated by arrow 108, to step 110 for the preparation of the medication according to the doctor's written order. Immediately upon preparing the medication per the doctor's order, the pharmacist then moves to the next step, as indicated by process arrow 114, to step 116, where the pharmacist prepares a label for the medication with additional information available to the patient through the healthcare facility's admission records or otherwise acquired, as may be appropriate. The prepared labels will include the patient's name, the patient's identification number, as assigned in the admissions procedure, the drug name, according to the preparation made by the pharmacist, the concentration, the concentration volume, the volume to be delivered and the infusion rate, if not calculated. The patient's height and weight may also be provided or other appropriate infusion data, if it is applicable to the therapy anticipated by the infusion. The pharmacist is provided with bar code specifications, to provide labels readable by the infusion pump.

The pharmacist then releases the container of the medication, as indicated by arrow 118, to be delivered to a nursing unit appropriately assigned to the indicated and identified patient, as indicated at step 120. The assigned nurse or other authorized healthcare professional then carries the medication container, as indicated by arrow 122, to the patient's room, bedside and infusion pump, as indicated by arrow 122, where a decision is to be made by the authorized healthcare professional to either scan the infusion information into the pump or to input the infusion data manually, as indicated by decision box 124. This advantageously provides the healthcare institution with the option to instruct authorized personnel to input the data manually or to scan the data in for improved administration capabilities provided by the bar code scanner. The healthcare institution may phase in the use of the scanner, or alternatively, may determine appropriate criteria for internal purposes for scanning certain types of infusion medications and not scanning others. In either event, the infusion pump desirably will be provided with recordation capabilities so that appropriate infusion data is recorded for administration purposes, for quality control purposes and, importantly, for purposes of the physician's review to determine appropriate continued or future treatment or medications for the patient. If the manual input mode is selected as indicated by arrow 126, then the nurse enters the infusion data from the control panel 22, as indicated by action block 128. When the automatic infusion data entry is determined to be appropriate, as indicated by arrow 130, the nurse then prepares the pump for bar code input, as indicated at step 132. Preparation of the pump for bar code input includes not only turning the pump on, as with a power button 56, but also setting the pump for the automatic bar code scanning mode. This may be done from a menu or otherwise depending upon the pump controls. When the pump is determined to be in the scan mode, as indicated by arrow 134, the nurse will be prompted to scan in a nurse's ID with a bar code on an ID tag (also made with a compatible bar code labeling system for use with the bar code module used in the device). Advantageously, all authorized healthcare professionals employed by the healthcare facility with qualifications for establishing an infusion to a patient, will be provided with an identification tag, badge, card or other coded identifier having a specialized authorization code. If the authorization code is present, the automatic bar code scanner may be initialized for establishing infusion data for a patient, as indicated by block 138. If the authorization code is not present or if the nurse does not scan in an appropriate ID, then the automatic system requires the nurse to exit the scan mode, as indicated by arrow 140. If infusion continues to be desired after the scan more is exited, then the nurse decides, at block 142, whether to move to the manual input mode, as indicated by arrow 144, thus moving the nurse back to block 128 for manually inputting data into the pump, or to start over with the scan mode initialization.

If the nurse's ID is properly scanned at 136 and if the authorization code is present in the scanned ID, as indicated by 138, then the bar code scanning software allows the nurse to proceed, as indicated by arrow 146. The nurse is prompted to scan in the patient's ID, at step 148. The patient's ID may appropriately be established with a wristband having a bar code for the patient's ID set forth thereon, or alternatively, where the patient's care limits the availability of using the wrist band for scanning purposes, the patient's ID may be on a patient card, a patient badge, or on the patient's chart, or other bedside available bar code so that proper patient identification is securely established. According to a preferred security check, a patient ID must be scanned in order for the automatic bar code scanning mode to continue. If the patient's ID is not scanned, as indicated by arrow 152, the nurse is then returned to decide whether to manually input the data into the pump, as at decision block 142 and manual input block 128, as described above.

If the patient ID is scanned, as indicated with arrow 154, the nurse will be prompted to scan in the infusion information from the container, as set forth in action block 156. The scanning of the information from the container would involve scanning the bag, bottle, syringe or other medication container past the bar code scanner window 64 with an appropriate confirmation that the scanning was completed, as by an audible sound signal or a visual signal. If the container information is readably scanned from the container, then the process would move forward, as indicated by arrow 158. If not, then, as indicated by return arrow 160, the nurse would be again returned to decision block 142 and manual input action block 128.

In the event that the information is appropriately bar code scanned from the container, then the bar code scanner module will convey the appropriate coded information to the pump software and to display the infusion data on the pump's visual display panel 34 and, preferably, in the portion of the display 40 where infusion data fields are established. The software also captures the infusion data for pump control in the event that all the infusion data can be appropriately validated by the healthcare professional. As indicated by arrow 166, indicating that the infusion data has been displayed, then the nurse must take required validation action, as set forth in step 168, thereby providing a further safeguard against inaccurate infusion data programmed into the pump control software. If the nurse cannot validate the input or any aspect of the input, then the system returns the nurse, as indicated by line 170, to exit the scan mode at 142 and to either move to the manual input 128 or otherwise correct the situation. Assuming the nurse can validate the accuracy of all the required input data as scanned, then the nurse initiates the infusion, as indicated by arrow 172 and action step 174.

Figure 4:
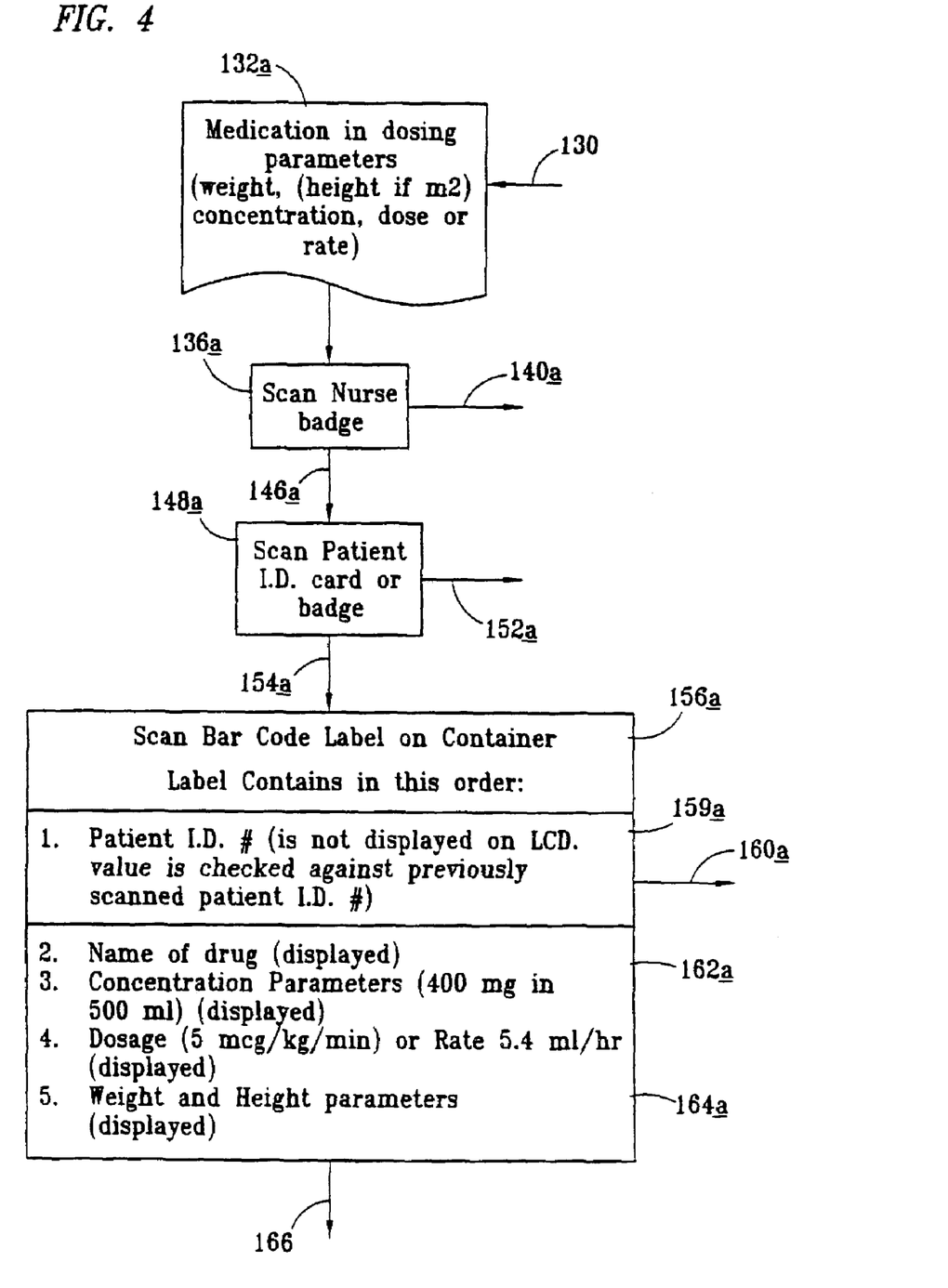
FIG. 4 is a schematic diagram of one alternative branch of the program flow diagram of the bar code reading security system of FIG. 3.
Figure 5:
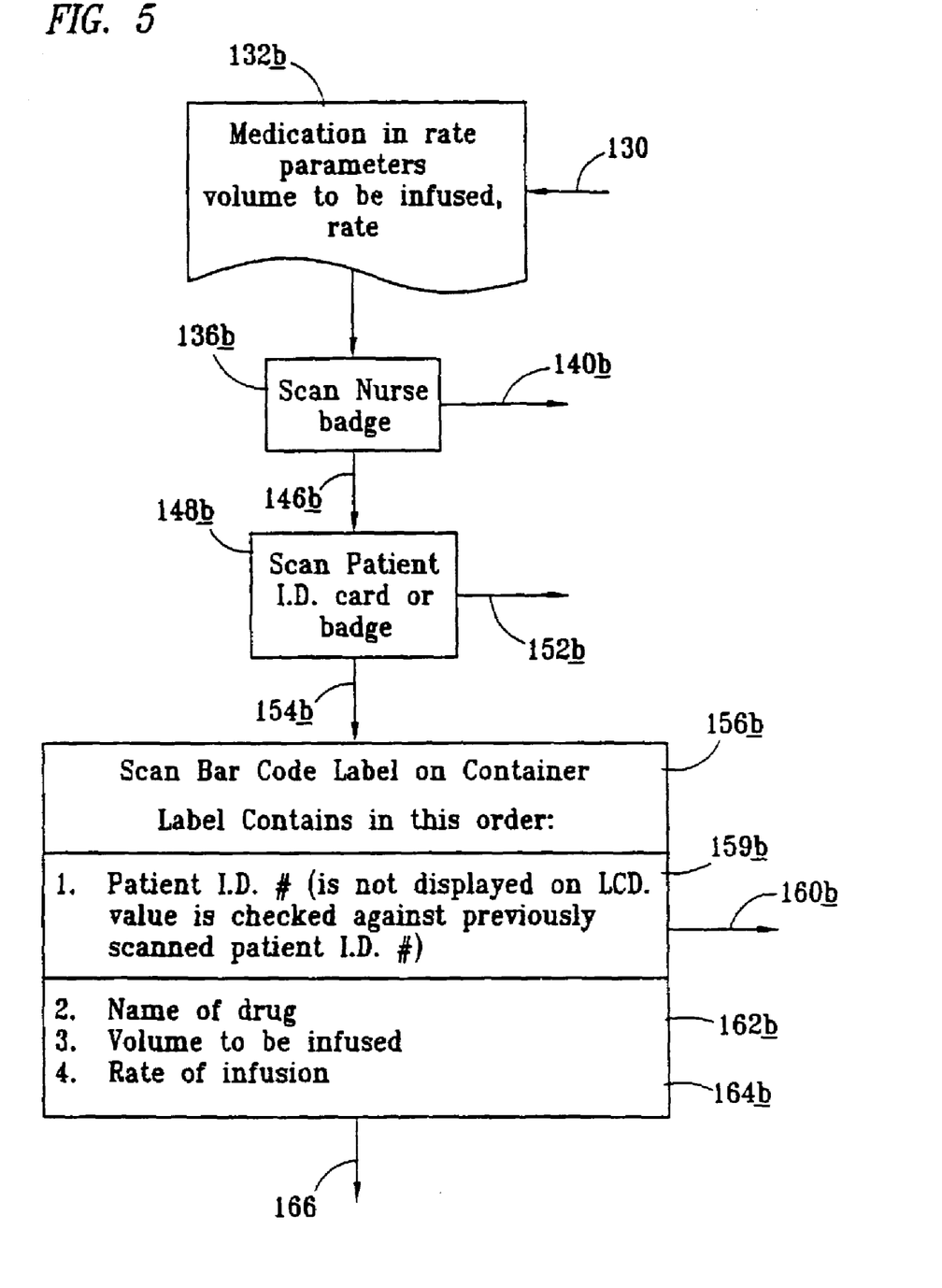
FIG. 5 is a schematic of another alternative branch of the program flow diagram of the bar code reading security system of FIG. 3.

With reference to FIGS. 4 and 5 each schematically depicting alternative variations of the steps 132–156 of the program flow diagram of FIG. 2 depending upon whether the label on the container provides medication in dosing parameters (represented in FIG. 4 as step 132*a*) or the medication is provided in rate parameter (shown in FIG. 5 as step 132b). In both instances alternative operation modes depicted in either FIG. 4 or FIG. 5 a nurse's badge must be scanned 136a or 136b respectively and if the nurse's ID is not scanned or authorization code is not present, path 140a or 140b moves the rate system to a manual mode. With appropriate scan of a nurse's badge the system moves either to path 146a or 146b to the step of scanning the patient ID or badge at either step 148a or 148b. Again, if the patient ID is not scanned then path 152a or 152b moving the system from the scan mode into the manual input mode. When the patient ID is appropriate scanned, then the system moves either along path 154a or 154b to the step 156a or 156b where the nurse scans the bar code label on the container for the appropriate infusion information. At that point, the system performs a comparison at step 159a or step 159b of the patient ID number with the scanned patient ID In either instance if the patient ID is not confirmed as matching identically then the system automatically exits the scan mode as indicated by path 160a or path 160b. Assuming the patient ID scan and that contained on the label bar code match, then the other information scanned from the container is displayed by the infusion pump at 162a or at 162b and appropriate control information for operating the pump is captured either as 164a or as 164b. It is at 162a and 162b that FIG. 4 and FIG. 5 differ as in FIG. 4 the dosing parameter shown at 162a and 164a include the name of the drug, the concentration parameters as for example 400 mg in 500 ml. The dosage as for example 5 mcg per kg/min or the rate such as 5.4 ml per hour and the weight and height parameters.

In FIG. 5 the rate parameter scan from the bar code label and displayed 162b and captured for operating the pump at 164b include the name of the drug, the volume to be infused, and the rate of infusion. Advantageously by having the alternative pathways available in a single pump, both standard methods for the doctor and the pharmacist to provide appropriate infusion information can be accommodated by a single pump appropriately programmed for bar code scanning according to the present invention. After the information is appropriately displayed, then the system moves along path 166 to require the nurse to validate the input at path 168 operating again as depicted in FIG. 2.

Figure 6:
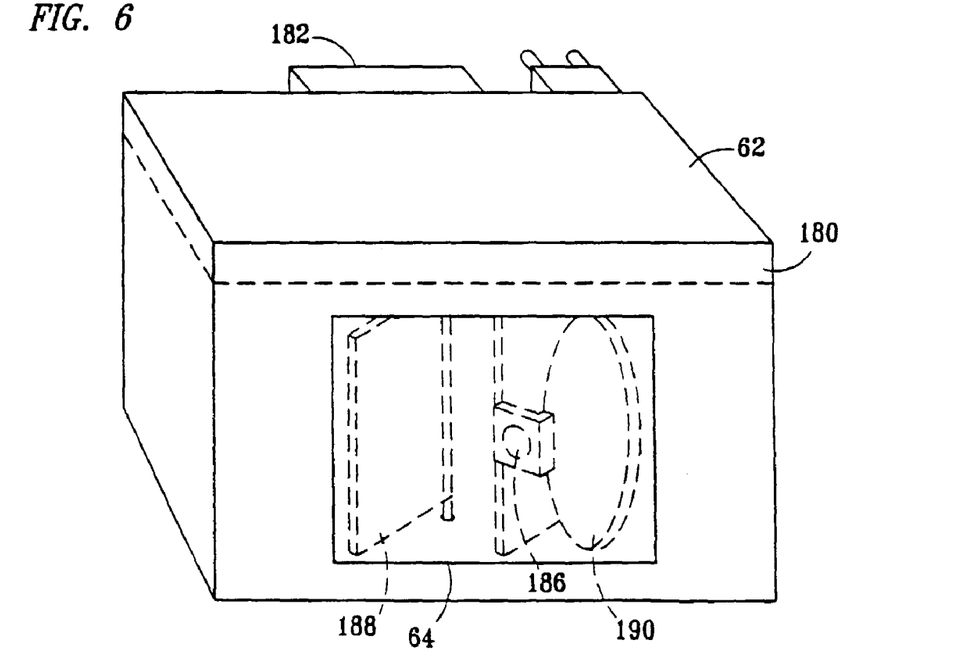
FIG. 6 is a schematic prospective view of a bar code reading module usefully incorporated into the infusion pumping device of the present invention.

FIG. 6 is a schematic perspective drawing of a bar code scanning module 62 that may be useful for purposes of the present invention to construct an infusion pump with a bar code scanner. Thus, the design of previously existing infusion pumps may be modified and adapted for the present invention with the addition of a bar code scanning module 62, such as that depicted in FIG. 6. Bar code scanning devices are now available in small dimensions, approximately one inch tall, one and one-half inches deep and two inches wide, with or without a decoder board, schematically depicted as block 180 in FIG. 6. The decoder software may be incorporated into the host infusion pump control software coupled as through an interface 182 into the infusion pump system. Such bar code scanning modules may, for example, be obtained from PSC Scanning, Inc., as for example, a product known as LM500 PLUS™. Such a scanning system may consist of the module and a decoder board, together with the host infusion pump control software. The module includes a housing 184 providing a scanner window 64 by which a laser emitting coherent visible light 186 operates together with a dithering mechanism 188 to emit coherent visible light that scans over the bar code label and is reflected to be gathered at collector lens 190.

A typical scanning system must be enabled with a trigger switch or a start switch to begin the reading process. The start switch, or in the present situation, the scan menu selection commands the module to begin scanning, providing both a "laser on" signal and also a signal to enable the dithering mechanism. The laser emits coherent visible light. When the bar code label with appropriate bar symbol is scanned, the module collects the light reflected from the symbol, amplifies and processes the reflected light and dark of the printed bar code label into a digital signal with appropriate timing that represents the bar code scan. The digital information is appropriately decoded, either by the decoder board or with the programming incorporated into the infusion pump. Upon initiating a scanning sequence, the dithering mechanism causes the emitted coherent light to sweep from one side to another, as for example, from left to right, and then back again. The sweeps will continue until a reflected valid bar code signal is collected through collector 190.

A typical decoder system might follow a three-step process in which the raw bar data is translated into decoded label data. A filter is applied to the data and then a preamble is placed in front of the edited label data and a post-amble may be added to the end of the edited label data. The data is then transmitted to the host infusion pump for display confirmation by the user, and control of the software. When a label is scanned into the device, it may be advantageous to provide audible "beep" to indicate that a valid bar code signal has been collected according to the bar code protocol used. Examples of acceptable bar codes may be a print-quality UPCA labels or C39 labels. For appropriate accuracy and size of label considerations, the C39 format has been found to be desirable for purposes of the present invention. The use of bar codes, including the use of filter characters before and after a label to separate the various fields of information to be provided in the single bar code label, is understood in the art and is beyond the scope of the present specification.

Thus, what has been disclosed is a medical infusion pump with bar code reading capabilities, designed for use in a hospital or other healthcare institution or facility. The medical infusion pump with the bar code reader also forms a part of a patient care system. The patient care system provides for an authorized pharmacist to prepare and label infusion fluids including medicines, drugs, and other pharmacological infusion products to be infused to patients upon doctor's orders. The labeling information may include patient ID, patient height, patient weight, drug information and drug administration dosage and rate information. The patient's doctor orders required medicines directly from the pharmacist and the pharmacist prepares the infusion fluid and labels the container from which the fluid will be infused to the patient. The invention relates particularly to labeling the containers not only with human readable printed label information but also with corresponding bar code information and to an infusion pump having an optional bar code reading mechanism and computer program system incorporated with the pump to permit authorized healthcare personnel and particularly nurses to scan the information into the pump. The authorized healthcare professional such as the nurse must scan in their own personal ID, their ID must include an authorization code to indicate their authorization to administer medicines to the patient. The authorized user must confirm the accuracy of the scanned information prior to administration of the medicine to the patient. Thus only an authorized healthcare giver or nurse is permitted to scan the pump operating information into the pump control software from the bar code and only after their ID is provided and they personally confirm the patient information as well as the drug administration information as it is displayed. Thus, the pump in the optional bar code reader mode of operation reads the information only when activated to do so and displays the scanned bar code information requiring an authorized nurse or other healthcare professional to be identified and their ID recorded and further requiring confirmation of the accuracy of selected scanned information prior to infusion.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A medical infusion pump having simplified and enhanced security features comprising:
    a pump housing;
    a pumping mechanism in the pump housing including electronic controls;
    a display screen on the pump housing;
    a manual entry control panel on the pump housing; control software operatively connected to the electronic controls of the pumping mechanism to operate the pumping mechanism according to input infusion data;
    a bar code reader contained in the pump housing and operatively attached to communicate scanned bar code infusion data to said display screen and to said control software, said bar code reader including means for data capture including capture of
    an authorized user code, an authorized user ID code; a patient ID code; and infusion operating control data; and the bar code reader further including means for activating the bar code reader to scan for the information to be captured including for an authorized user code, for an authorized user ID code, for a patient ID code, and for medicinal infusion operating data including intended patient ID data; and
    means for automatically confirming a match of the scanned authorization code to an acceptable authorization code and for confirming a match of the scanned patient ID code to the intended patient ID in the scanned medicinal infusion data before operating the infusion pump according to said medicinal infusion data; and
    a display and control program connected to the bar code reader and the display panel to display the scanned infusion data and requiring manual entry by the authorized user to validate the displayed medicinal infusion data prior to activating said pump mechanism to infuse medicines according to said scanned infusion data.

2. The medical infusion pump of claim 1 further comprising:
    means for manually controlling the infusion pumping operation from the manual control panel; and
    means for selecting between the barcode reader for entry of infusion data to control infusion by the pump and the manual control panel for entry of the infusion data to control infusion by the pump.

3. The medical infusion pump of claim 1 further comprising means for automatically requiring a scanned authorized user ID code before operating the infusion pump according to said medicinal infusion data.

4. A medical infusion pump bar code reading system having simplified and enhanced security features comprising:
    an infusion pump with a housing, a control display screen and control software for operating the infusion pump according to input infusion data;
    a bar code reader contained in said infusion pump housing and operatively attached to communicate scanned bar code infusion data to said control display screen and to said control software;
    means for manually controlling the infusion pumping operation from the manual control panel; and
    means for selecting between the barcode reader for entry of infusion data to control infusion by the pump and the manual control panel for entry of the infusion data to control infusion by the pump,
    a bar code scanning program means for barcode scanning connected through circuitry in said pump, said bar code scanning program having means for activating said bar code reader to scan for an authorized user code, and for an authorized user ID code from a user's badge, tag, card, or coded identifier, for a patient ID code from a patient's wrist band, card, chart, or badge, and for infusion data including a patient ID code from a medicinal fluid container label, said infusion data for operating said infusion pump;
    a confirmation program means for requiring acceptable scanning of an authorization code and an authorized user ID code and for comparing a scanned patient ID from a patient coded identifier, wrist band, tag, or badge to a patient ID from a medicinal fluid container label to confirm a match before operating the infusion pump according to said infusion data; and
    a display program means for displaying said infusion data and further requiring manual keypad confirmation of required pump operating infusion data by the authorized user prior to activating said pump to infuse medicines according to said scanned infusion data.

5. An enhanced medical infusion pump bar code reading system for use in a medical facility, said system comprising:
    an infusion pump having a display screen and software-programmed controls with predetermined infusion capabilities and compatible with predetermined infusion fluids in appropriate containers;
    pharmacist label preparation software and mechanism by which labels with bar code infusion information and corresponding human readable information according to a validated doctor's prescription, is prepared and placed on an appropriate infusion fluid container by a pharmacist;
    a bar code reader operatively connected to said display screen of said infusion pump and to said software-programmed controls for receiving scanned infusion data from the bar code label on an appropriate container of infusion fluid for permitting the bar code scanning of infusion data only by an authorized user upon scanning of an authorized user code and for displaying the scanned infusion data; and
    means for validation of said displayed infusion data by an authorized user and for communicating said infusion data to said software controls of said pump upon the manual validation by the authorized user and to operate the infusion pump according to said scanned infusion data only upon validation of said scanned infusion data.

6. An enhanced medical infusion pump bar code reading system as in claim 5, further comprising a nurse's badge, tag, card, or coded identifier having a bar code authorization code and a bar code identification code readable by said bar code reader, and a confirmation program operatively coupled to said pump for preventing operation of said pump according to scanned infusion data unless both said authorization code and said user identification code are scanned.

7. An enhanced medical infusion pump bar code reading system as in claim 5, further comprising a patient wrist band, card, chart, or identification badge, with a bar code patient ID thereon, and a portion of a bar code label on an appropriate fluid container comprising a patient identification code, and a confirmation program operably coupled to said pump for preventing operation of said pump according to said scanned infusion data unless said patient ID code scanned from said patient's wrist band, card, chart, or badge matches said patient identification code scanned from said label.

* * * * *